United States Patent [19]

Burrage

[11] 4,085,755
[45] Apr. 25, 1978

[54] URINARY DRAINAGE BAG

[76] Inventor: Benjamin Stuart Burrage, 94 Lingarde Dr., Scarborough, Ontario, Canada, M1R 1X9

[21] Appl. No.: 829,965

[22] Filed: Sep. 1, 1977

Related U.S. Application Data

[63] Continuation-in-part of Ser. No. 681,394, Apr. 29, 1976, abandoned.

[51] Int. Cl.² .................................................. A61F 5/42
[52] U.S. Cl. ................................... 128/295; 128/272; 128/275; 128/214 D; 128/DIG. 24
[58] Field of Search ............... 128/272, 275, DIG. 24, 128/294, 295, 214 D; 53/187; 150/8, 9

[56] References Cited

U.S. PATENT DOCUMENTS

| 3,186,410 | 6/1965 | Buono | 128/275 |
| 3,574,868 | 4/1971 | McWhorter | 128/295 |
| 3,901,235 | 8/1975 | Patel et al. | 128/275 |
| 3,991,912 | 11/1976 | Soto | 128/DIG. 24 |

Primary Examiner—Kyle L. Howell
Assistant Examiner—Henry S. Layton

[57] ABSTRACT

The specification describes a fluid drainage bag having first and second plies, a fold in the first ply, and a drainage opening closed by a flap valve in the fold. The fold is held open by means of a flexible drainage tube maintained in a flexed position between the fold and the upper end of the bag. The opening of the fold draws the flap valve away from the second ply so that it does not stick in the open position to the second ply.

9 Claims, 4 Drawing Figures

U.S. Patent          April 25, 1978          4,085,755
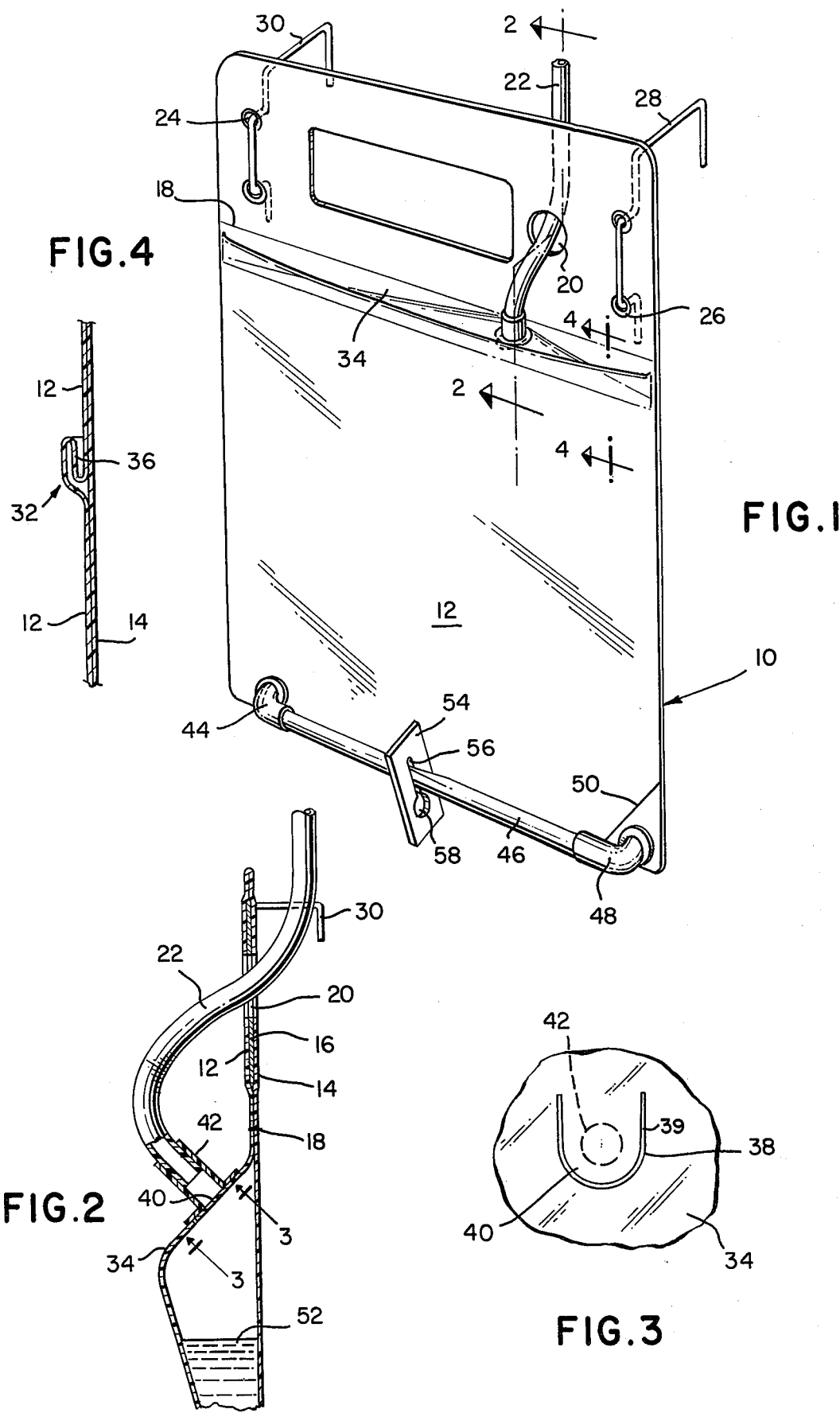

URINARY DRAINAGE BAG

This application is a Continuation-in-Part of Ser. No. 681,394 filed Apr. 29, 1976, now abandoned.

FIELD OF THE INVENTION

This invention relates to fluid drainage bags and to urinary drainage bags in particular.

BACKGROUND OF THE INVENTION

Many patients in hospitals, nursing homes, and other institutions, have need for urinary drainage devices. Present devices commonly consist of a flexible tube connected to a catheter or the like, attached to the parient. Urine drains from the catheter through the flexible tubing and is deposited in a urinal bag, which is subsequently drained.

On some bags, a check valve is provided at the inlet to the bag to prevent reverse flow of the urine through the tube. However, due to the shape of the conventional bag and as a result of the bodily movement of the connected patient, the bag generally collapses to close off the flap valve or the inlet is twisted to prevent the flap valve from communicating with the flexible tube, thereby presenting obvious difficulties.

Furthermore, presently used urinary drainage bags generally have very poor drainage due to the numerous liquid traps which are the result of poor bag construction.

According to the present invention, a fluid drainage bag comprises a first ply, a second ply, a fold in the first ply, a hollow fitting provided at the fold and forming a drainage opening through the first ply into the bag, a resilient self-closing flap valve for closing the drainage opening, a flexible drainage tube secured to the fitting and means for flexing a portion of the drainage tube between the fitting and the upper end of the bag. The flexed portion of the drainage tube opens the fold and draws the flap valve away from the second ply to permit free opening of the flap valve in a manner such that it does not stick in the open position to the second ply. The arrangement is also such that the fitting is inclined from the horizontal and the flap valve is inclined from the vertical, so that fluid draining through the drainage tube, flows down through the fitting onto the flap which opens under the weight of the fluid.

BRIEF DESCRIPTION OF THE DRAWINGS

The above, as well as other advantages and features of the present invention will become apparent from the following detailed description of the preferred embodiments wherein:

FIG. 1 is a perspective view of the urinary drainage bag of the present invention;

FIG. 2 is a cross-sectional view taken substantially along the plane indicated by line 2—2 of FIG. 1;

FIG. 3 is a cross-sectional view taken substantially along the plane indicated by line 3—3 of FIG. 2; and FIG. 4 is a cross-sectional view taken substantially along the plane indicated by line 4—4 of FIG. 1.

DETAILED DESCRIPTION OF THE PREFERRED EMBODIMENTS

Referring to the drawings, wherein like numerals indicate like elements throughout the several views, the urinary drainage bag 10 of the present invention includes front ply 12 and rear ply 14 of plastic material.

Adjacent the top of bag 10, the front and rear plies are reinforced by a plate 16 disposed between the plies and held in place by welded seam 18, which secures the plies together to form a pocket for plate 16. Plate 16 includes a hole 20 therethrough which is also complemental with a hole in the front and rear plies so that a length of drain tube 22 connected to a catheter or the like can be projected through hole 20 from the rear of the bag and supported by plate 16.

Plies 12 and 14 are also provided with holes 24 and reinforcing grommets 26 at their lateral ends adjacent the top of bag 10 to receive hooks 28 and 30, which are used to hang bag 10 on a convenient support, such as a hospital bed. Below each hook 28 and 30, the lateral corners of the front ply 12 of bag 10 are doubled back upon themselves in an upward and downward direction as shown at 32 in FIG. 4, thereby providing a fold 36 in the front ply of the bag.

Fitting 42 is secured to the outer surface of ply 12 at the bag fold. The center portion 34 of the fold is cut by a U-shaped slit 38 to form a flap valve 40 integral with ply 12. The flap valve is located adjacent to and larger than the end of fitting 42 which provides a drainage opening into the bag. In providing the slit a very minor portion of the fold is removed as by a hot wire to assume that there is clearance between the bag ply and the flap valve for easy opening of the valve. This clearance is shown at 39 in FIG. 3. Drainage tube 22 is secured to the other end of fitting 42.

Drainage tube 22 has an overall length which permits movement of the patient without disturbing the bag, therefore although it is not shown in the drawings there is approximately 4 to 5 feet of drainage tube between the bag and the patient.

As shown in FIG. 2, a minor portion of the tube is flexed between plate 16 and fitting 42. The side wall of the tube frictionally engages the plate as it passes through aperture 20, thereby precluding the tube from slipping through the aperture.

Tube 22 is highly flexible over long lengths, however resistance to bending is substantially increased over the short length of tube trapped between the plate and the fitting and in an attempt to straighten itself the short portion of flexed tube pulls on fitting 42 to open the fold and separate the front ply from the rear ply of the bag as shown in FIG. 2. Furthermore, fitting 42 preferably has a somewhat more rigid construction which precludes it from bending when the fold is open thereby enhancing the flexing action of the tube.

As can be appreciated other constructions could easily be used for maintaining a flexed portion of tube between the upper end of the bag and the front ply for opening the bag fold. Such other constructions could include any type of securing means frictionally engaging the sidewall of the drainage tube. These securing means could not of course clamp the drainage tube to the extent that the flow of liquid therethrough would be restricted.

With the fold thusly open, it can be readily seen that fitting 42 is inclined from the horizontal so that fluid continues its downward flow from the drainage tube through the fitting. In addition, flap valve 40 which is self closing is inclined from the vertical so that the flap opens under the weight of the fluid flowing through the fitting 42. It will also be noted that fitting 42 is straight fitting and that there are no liquid traps between the patient and the drainage bag.

One of the main difficulties encountered in the past in cases of drainage bags provided with flap valves, has been that the flap valves often adhere due to capillary attraction to the opposing ply of the bag, because there is little or no separation between the bag plies. This of course results in an open valve which permits the flow of fluid from the bag back to the drainage tube. According to the present invention, the likelihood of such an occurrence is highly improbable, because of the separation of the plies in the area of the flap valve. This permits free opening of the valve without interference with the rear ply of the bag. As can be seen from the drawings, it would require considerable bending of the flap for the flap to come into contact with the rear bag ply and the memory of the flap material would be more that adequate to compensate and overcome any possible capillary attraction between the flap valve and the rear ply. This of course is not the case with conventional bags in which the flap valve is in a vertical orientation essentially in contact with the opposing bag ply.

Connected to the lower corner of front ply 12 is an elbow 44 in communication with the interior of bag 10. Elbow 44 mounts a flexible rubber bag drain tube 46, which when not in use is pushed in a second elbow 48 connected to the opposing corner of front ply 12, sealed along seam 50 to the rear ply 14 so as not to be in communication with the fluid contents 52 deposited between plies 12 and 14 of bag 10.

A clamp member 54 having an elongated slot 56 for squeezing tube 46 shut, is normally positioned on tube 46. Slot 56 terminates in a round hole 58 which when clamp 54 is moved so that hole 58 surrounds the tube 46 and tube 46 is moved from elbow 48, the contents 52 of bag 10 can be drained through tube 46.

In use, contents 52 will drain through tube 22 down tube 42 through flap valve 40 and into the interior of the bag. The fluid contents 52 can then be drained through elbow 44 and tube 46 to a suitable receptacle. The weight of the fluid contents in bag 10 tends to extend the distance between plies 12 and 14, pulling fitting 42 and flap valve 40 towards a vertical and horizontal position, respectively, rather than tending to close flap valve 40 against rear ply 14.

Although various preferred embodiments of the invention have been described herein in detail, it will be apparent to one skilled in the art that variations may be made thereto without departing from the spirit of the invention or the scope of the appended claims.

The embodiments of the invention in which an exclusive property or privilege is claimed are defined as follows:

1. A fluid drainage bag comprising a first ply, a second ply, a fold in said first ply, a hollow fitting provided at said fold and forming a drainage opening through said first ply into said bag, a resilient self closing flap valve for closing said drainage opening, a flexible drainage tube secured to said fitting and means for flexing a portion of said drainage tube between said fitting and the upper end of said bag, the flexed portion of said drainage tube opening said fold and drawing said flap valve away from said second ply to permit free opening of the flap valve in a manner so as to preclude sticking in the open position to the second ply, the arrangement being such that said fitting is inclined from the horizontal and said flap valve is inclined from the vertical so that fluid draining through said drainage tube flows down through said fitting onto said flap valve which opens under the weight of the fluid.

2. A fluid drainage bag as claimed in claim 1 wherein said fitting is stiff to preclude bending of same during opening of said fold.

3. A fluid drainage bag as claimed in claim 2 wherein said fitting is a straight fitting to preclude trapping of fluid therein.

4. A fluid drainage bag as claimed in claim 1 wherein said flap valve is larger than said drainage opening and is intregal with said first ply.

5. A fluid drainage bag as claimed in claim 1 wherein said means for flexing a portion of said drainage tube comprises an aperture provided in a plate at the upper end of said bag, said aperture frictionally engaging the sidewall of said drainage tube thereby precluding movement of said drainage tube in said aperture.

6. A fluid drainage bag as claimed in claim 5 wherein said plate is provided between said first and second plies for reinforcing said bag.

7. A fluid drainage bag as claimed in claim 1 including hook means for hanging said bag on a support and fluid drainage means for draining fluid from said bag.

8. A bag as claimed in claim 7 wherein said fluid draining means comprises a flexible tube extending from the interior of said bag and a clamp on said tube to pinch and close said tube when not in use.

9. A bag as claimed in claim 4 wherein a clearance is provided along the edge of said flap valve between said flap valve and said first ply.

* * * * *